United States Patent

Wallner et al.

[11] Patent Number: 5,814,101
[45] Date of Patent: Sep. 29, 1998

[54] HOLDER FOR HEART VALVE PROSTHESIS

[75] Inventors: Margaret A. Wallner, Forest Lake; David R. Elizondo, St. Paul; Kimberly A. Anderson, Eagan; Guy P. Vanney, Blaine; Kurt D. Krueger, Stacy; Michael J. Girard, Lino Lakes; Stephen A. Petersen, Eagan; Darrin J. Bergman; Terry L. Shepherd, both of Shoreview, all of Minn.

[73] Assignee: St. Jude Medical, Inc., St. Paul, Minn.

[21] Appl. No.: 719,568

[22] Filed: Sep. 25, 1996

[51] Int. Cl.[6] .................................. A61F 2/24; A61M 5/00
[52] U.S. Cl. ........................... 623/2; 623/66; 606/1
[58] Field of Search .................. 623/2, 3, 66, 900; 606/1, 7, 99, 205–211

[56] References Cited

U.S. PATENT DOCUMENTS

| 3,546,710 | 12/1970 | Shumakov et al. ............... 3/1 |
| 3,574,865 | 4/1971 | Hamaker ........................... 3/1 |
| 3,828,787 | 8/1974 | Anderson et al. ............... 128/303 |
| 3,860,005 | 1/1975 | Anderson et al. ............... 128/303 |
| 4,655,218 | 4/1987 | Kulik et al. .................... 128/321 |
| 4,683,883 | 8/1987 | Martin ............................ 128/303 |
| 4,755,181 | 7/1988 | Igoe ............................... 623/2 |
| 4,865,600 | 9/1989 | Carpentier et al. .............. 623/2 |
| 4,932,965 | 6/1990 | Phillips ........................... 623/2 |
| 5,041,130 | 8/1991 | Cosgrove et al. ................ 623/2 |
| 5,071,431 | 12/1991 | Sauter et al. .................... 623/2 |
| 5,163,954 | 11/1992 | Curcio et al. ................... 623/2 |
| 5,236,450 | 8/1993 | Scott ............................... 623/2 |
| 5,289,817 | 3/1994 | Williams et al. ................. 128/20 |
| 5,290,300 | 3/1994 | Cosgrove et al. ................ 623/2 |
| 5,339,802 | 8/1994 | Cook ............................... 128/20 |
| 5,370,685 | 12/1994 | Stevens .......................... 623/2 |
| 5,403,305 | 4/1995 | Sauter et al. .................... 606/1 |
| 5,423,887 | 6/1995 | Love et al. ...................... 623/2 |
| 5,425,705 | 6/1995 | Evard et al. ..................... 604/28 |
| 5,433,700 | 7/1995 | Peters ............................. 604/4 |
| 5,443,502 | 8/1995 | Caudillo et al. ................. 623/2 |
| 5,531,785 | 7/1996 | Love et al. ...................... 623/2 |
| 5,571,215 | 11/1996 | Sterman et al. ................. 623/2 |
| 5,578,076 | 11/1996 | Krueger et al. ................. 623/2 |
| 5,582,607 | 12/1996 | Lackman ......................... 623/2 |

FOREIGN PATENT DOCUMENTS

| 91 04 383.2 | 6/1991 | Germany . |
| 990220 | 1/1983 | U.S.S.R. . |
| 1690738 A1 | 4/1989 | U.S.S.R. . |
| 8705489 | 9/1987 | WIPO ............................ 623/2 |
| WO 94/18881 | 9/1994 | WIPO . |
| WO 95/15715 | 6/1995 | WIPO . |
| WO 95/17139 | 6/1995 | WIPO . |

*Primary Examiner*—Michael J. Milano
*Assistant Examiner*—Tram Anh T. Nguyen
*Attorney, Agent, or Firm*—Westman, Champlin & Kelly, P.A.

[57] ABSTRACT

A holder for engaging a heart valve prosthesis during implantation includes a holder body and stem. The stem is adapted to receive a handle used to manipulate the prostheses during implantation. The stem is moveable between a standard implantation position and a low profile delivery position.

18 Claims, 11 Drawing Sheets

HOLDER FOR HEART VALVE PROSTHESIS

FIELD OF THE INVENTION

The present invention relates to devices for implanting heart valve prostheses. More specifically, the invention relates to a low profile holder which holds a heart valve prosthesis during implantation.

BACKGROUND OF THE INVENTION

Holders for holding and supporting heart valve prostheses during shipping and implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Traditionally, heart valve replacement surgery is an involved procedure in which a sternotomy is performed and the chest cavity of the patient must be widely opened to provide access to the patient's heart. This provides a surgeon with direct unobstructed access to the heart. In such a procedure, the prosthesis is typically held at the end of an elongated handle which is aligned with the axis of the prosthesis. However, this procedure requires a prolonged patient recovery period to recover from the trauma suffered to the upper torso.

Minimally invasive procedures have been developed wherein open heart surgery is performed through small incisions which eliminate the need for a traditional sternotomy. One such procedure is described in International Publication No. WO 94/18881, entitled METHOD FOR PERFORMING THORASCOPIC CARDIAC BYPASS PROCEDURES and WO 95/15715, entitled DEVICES AND METHODS FOR INTRACARDIAC PROCEDURES. In this procedure, elongated tools and/or trocars may be used to operate on the heart. As discussed in Publication Nos. 94/18881 and 95/15715, this procedure can be used during heart valve replacement.

In general, minimally invasive implantation requires minimal rib spreading and implantation through a small opening. This places an emphasis on the need for a more low profile holder and does not involve the significant chest trauma associated with traditional open heart surgery. One advantage of this procedure is that the recovery period for the patient can be reduced significantly. Furtner, heart valve prostheses are typically carried in packaging which is not designed for a low profile holder. Thus, such packaging can not be used with low profile holders.

SUMMARY OF THE INVENTION

A holder for engaging a heart valve prosthesis during implantation includes a holder body and a stem. The stem is adapted to receive a handle used to manipulate the prosthesis during implantation. The stem is moveable between a standard implantation position and a low profile delivery position. In one embodiment, the stem articulates about a pivot which couples the stem to the holder body. Other embodiments of the invention include a locking mechanism to maintain a position of the stem relative to the holder body.

DETAILED DESCRIPTION OF THE PREFERRED EMBODIMENTS

The present invention relates to a device which is used to position a heart valve prosthesis during implantation. The implantation may be through minimally invasive surgery, such as when performed through an incision smaller than that which is required for a traditional sternotomy, or using a more traditional implantation technique in which the axis of the valve is generally parallel with the axis of the handle to which it is attached during valve delivery. For purposes of this description of the invention, the device will be described generally with regard to its use with a bi-leaflet mechanical heart valve which has an annulus with a substantially annular aperture. Such a heart valve prosthesis is available from St. Jude Medical, Inc. of St. Paul, Minn. However, it will be understood that the invention is applicable to other types of replacement heart valves or repair devices, including other mechanical heart valves, bioprosthetic valves and annuloplasty rings. One type of low profile holder is described in co-pending U.S. Pat. application Ser. No. 08/449,145, filed May 24, 1995 entitled LOW PROFILE HOLDER FOR HEART VALVE PROSTHESIS which is commonly assigned with the present application.

Figure 1:
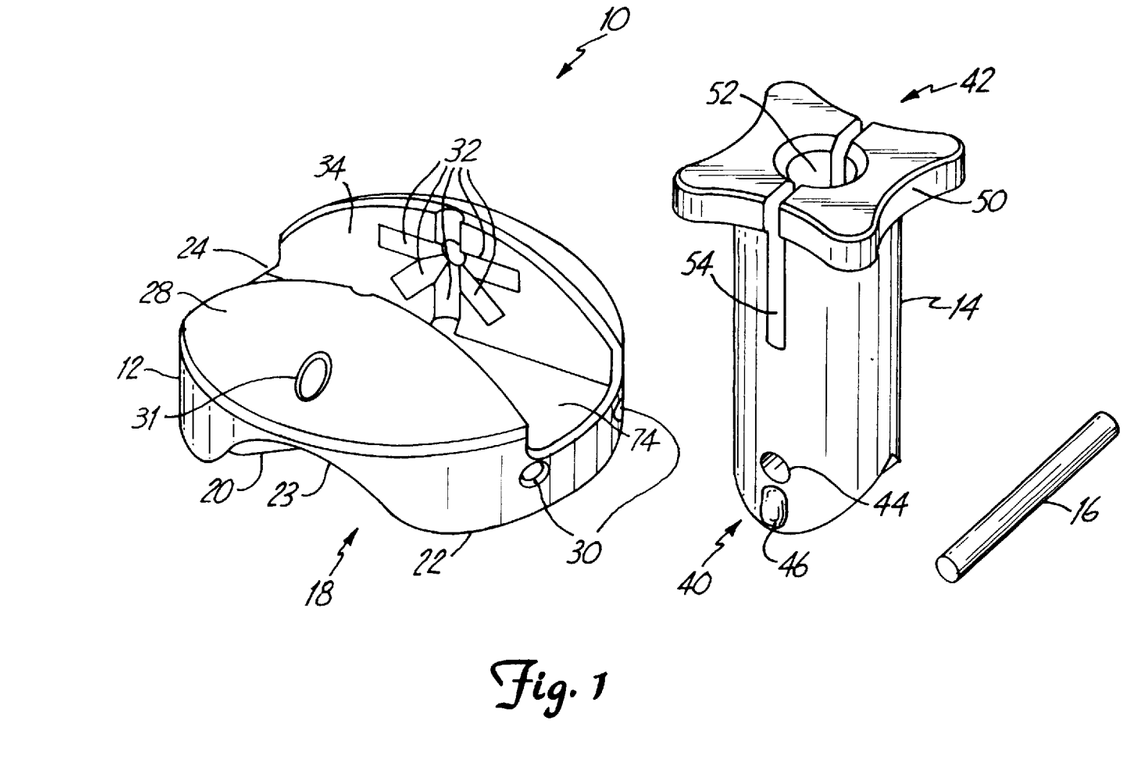
FIG. 1 is an exploded perspective view of a positionable holder in accordance with one embodiment of the invention.

FIG. 1 is an exploded perspective view of a positionable holder 10 in accordance with one embodiment of the present invention. It will be understood that the holder of the present invention may be adapted for use with any type of prosthesis including mechanical and bioprosthetic valves, and repair devices, including annuloplasty rings, and such adaptation is considered to be within the scope of the present invention. Further, it will be understood that the invention may be used with both aortic and mitral mechanical heart valves.

Positionable holder 10 includes holder body 12, holder stem 14 and pivot pin 16. Holder body 12 includes a heart valve prosthesis engaging (distal) side 18 which provides occluder conforming surfaces 20, rim 22 and pivot guard receptacles 23. Distal side 18 is adapted to generally conform to a mitral heart valve prosthesis, although distal side 18 may be adapted for use with an aortic valve. In the particular embodiment shown, occluders of the prosthesis are held in a substantially closed position such that they are protected within a body of the prosthesis during delivery and implantation. Holder body 12 includes open portion 24 formed in proximal face 28. Suture openings 30 and pin receptacle 31 are formed through holder body 12. Positioning detents 32 are formed in side walls 34 formed by open portion 24.

Holder stem 14 includes distal end 40 adapted for coupling to holder body 12 and proximal end 42 adapted for coupling to a handle (not shown in FIG. 1) Distal end 40 includes pin receptacle 44 and positioning protrusion 46. Proximal end 42 includes finger grips 50, handle opening 52 and slot 54. Finger grips 50 may be grasped by fingers of a surgeon and used to manipulate the prosthesis and apply torque to the prosthesis during the implantation procedure.

Holder body 12, stem 14 and pivot pin 16 are assembled such that pin receptacles 31 and 44 are aligned and stem 14 is secured to holder body 12 with pivot pin 16 through receptacles 31 and 44. Thus, stem 14 articulates relative to holder body 12 about pivot pin 16. Positioning protrusion 46 is shaped to generally conform to positioning detents 32 such that stem 14 is locked in position relative to holder body 12 in one of positioning detents 32. In the particular embodiment shown in FIG. 1, positioning detents 32 provide five different locking positions. However, any number of detents at any desired position may be employed.

Positionable holder 10 is typically shipped with stem 14 at a 90° angle relative to the plane that includes the annulus formed by holder body 12, i.e., parallel to the axis of the prosthesis. As used herein, "standard implantation position" refers generally to the position used to implant a prosthetic heart valve through traditional implantation techniques such as a sternotomy. Stem 14 can be articulated about pivot pin 16 such that it is aligned substantially parallel with the plane that includes the annulus of holder body 12 and generally perpendicular to the axis of the prosthesis. As used herein, "low profile delivery position" refers generally to the position which is useful in minimally invasive implantation techniques in which the heart valve prosthesis is delivered through a small opening and implanted in the patient. Generally, an elongated handle is adapted to be received in handle opening 52 of stem 14. Pins carried on the handle are received in slot 54 such that torque may be transmitted from the handle to the stem to thereby rotate the heart valve. However, the invention may be used with any type of handle having any appropriate coupling mechanism for coupling to stem 14. During a minimally invasive implantation, after the prosthesis is inserted into the chest cavity, where it was inserted in a low profile delivery position, the holder body 12 can be pivoted using an appropriate elongated surgical instrument such that it is moved into the appropriate implantation position and properly presented to the natural tissue annulus of the patient's heart.

Figure 2A:
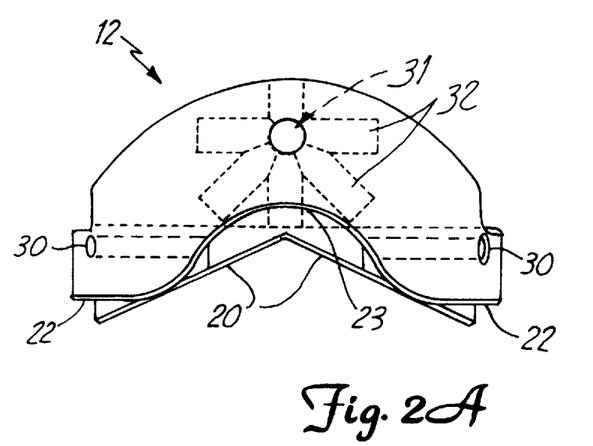
FIGS. 2A and 2B are side views and bottom plan views, respectively, of a holder body shown in FIG. 1.
Figure 2B:
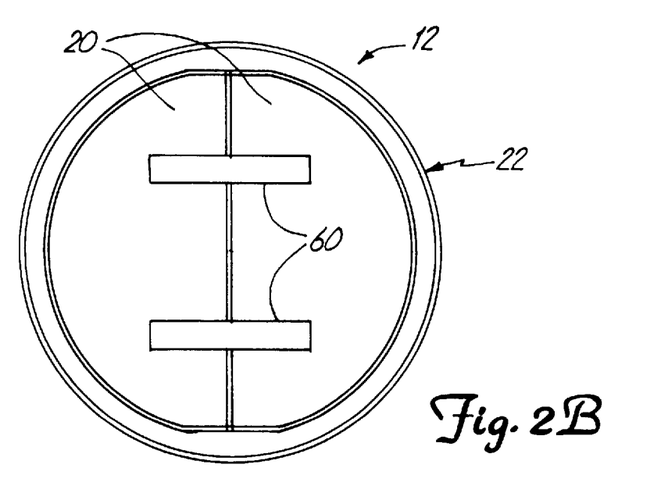

FIGS. 2A and FIG. 2B are side and bottom plan views, respectively, of holder body 12. Suture openings 30 extend through body 12 to suture slot 60 shown in FIG. 2B. A suture may be threaded through openings 30 so that the sutures are positioned to apply a small amount of pressure to occluders of the prosthesis to maintain the occluders in a closed position. Further, such sutures may be used to couple the prosthesis (not shown) to the holder body by stitching the sutures through a suture cuff of the prosthesis. After the prosthesis has been secured to the tissue annulus of the patient's heart, the sutures are cut such that The positionable holder 10 may be withdrawn from the chest cavity.

Figure 3A:
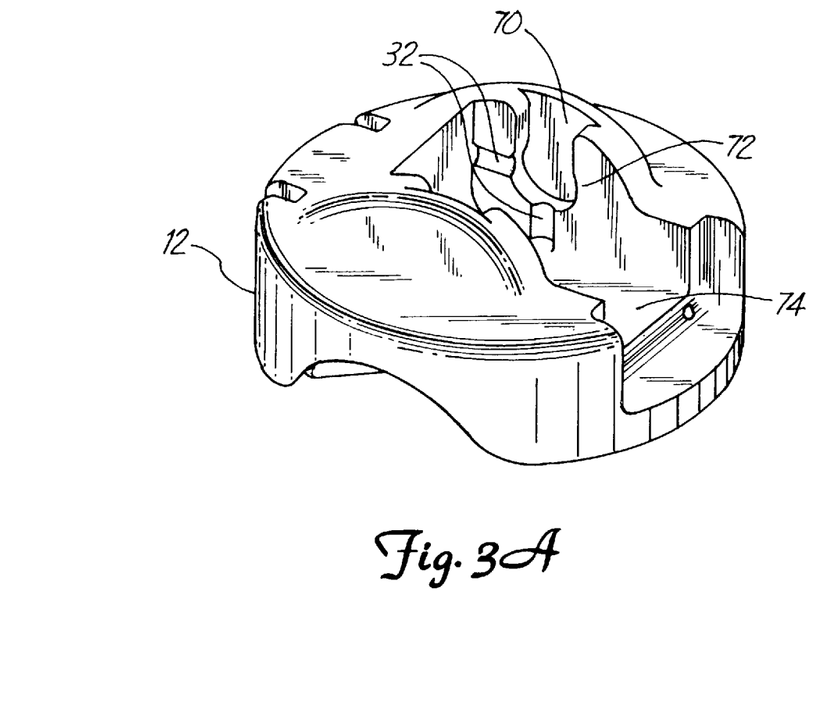
FIGS. 3A and 3B show perspective views of one embodiment of a holder body and a stem, respectively.
Figure 3B:
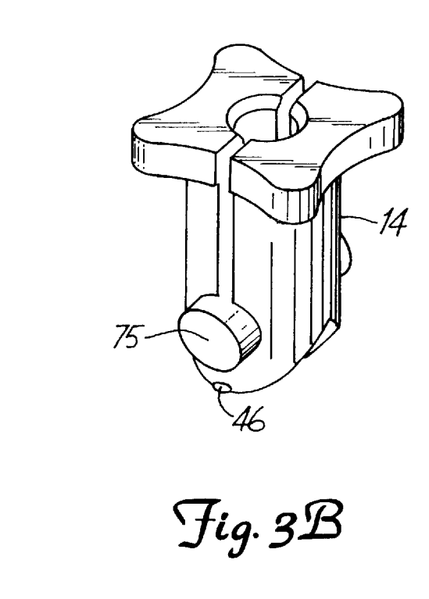

FIGS. 3A and 3B show perspective views of another embodiment of a holder body 12 and stem 14, respectively, in accordance with the invention. Generally, where possible, similar numbers have been used to identify similar elements in this description. Holder body 12 of the embodiment of FIG. 3A includes slot 70 and pivot 72. Holder 14 of FIG. 3B includes snap fit pin 75 adapted to be received in pivot 72. Detent 32 maintains stem 14 in either the standard implantation or low profile delivery position by engagement with positioning protrusion 46. Stop 74 (see FIG. 1) of holder body 12 prevents rotation of stem 14 past the low profile implantation location.

Figure 4A:
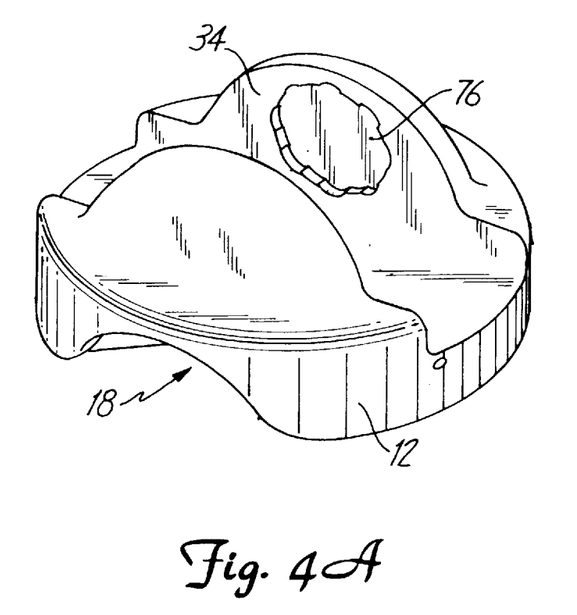
FIGS. 4A and 4B show perspective views of one embodiment of a holder body and a stem, respectively.
Figure 4B:
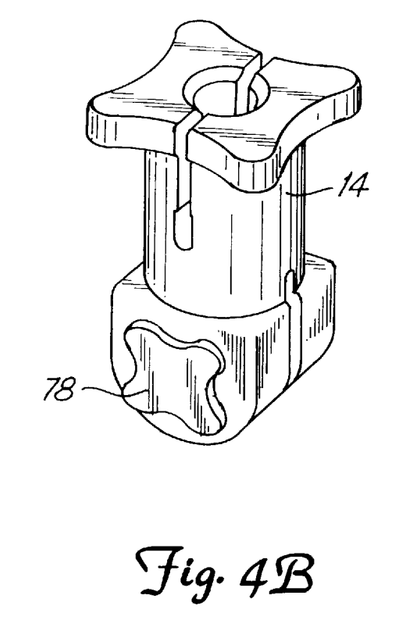

FIG. 4A is a perspective view of holder body 12 and FIG. 4B is a perspective view of stem 14 in accordance with another embodiment. In the embodiment of FIG. 4A, side wall 34 includes octagonal pivot recess 76 which is adapted to receive star shaped protrusion 78 of stem 14 shown in the perspective view of FIG. 4B. In this embodiment, the stem may be positioned generally at angles of 0°, 45°, 90°, 135° and 180° relative to holder body 12 and the hexagonal shape of recess 76 provides a locking mechanism in these positions.

Figure 5A:
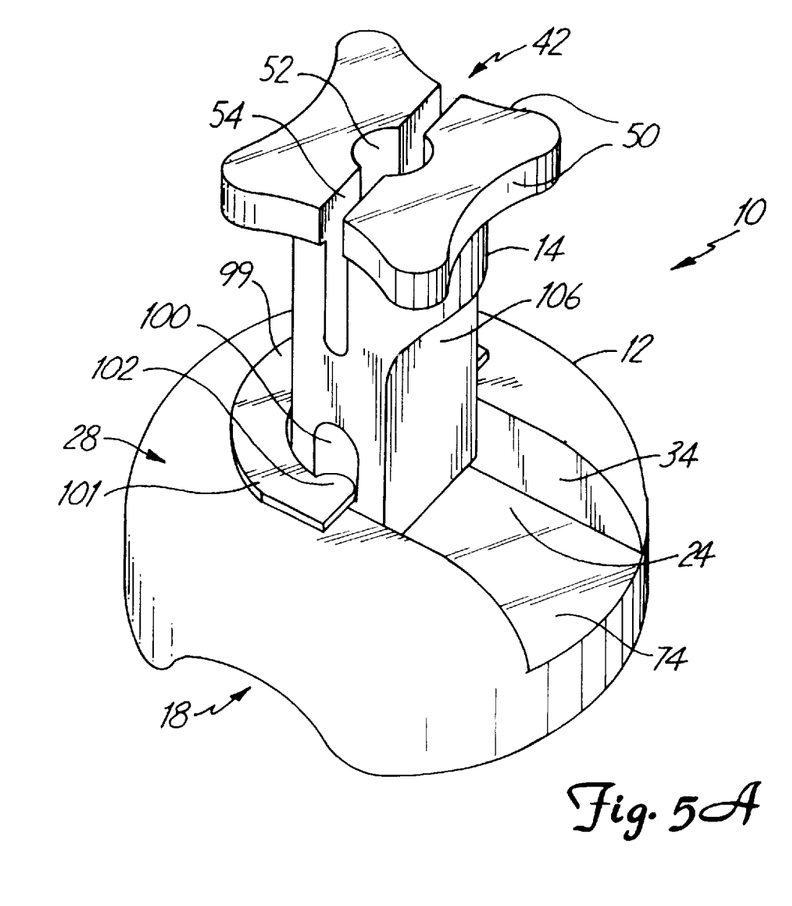
FIG. 5A is a top perspective view of a positionable holder in accordance with another embodiment shown in a standard implantation position.

FIG. 5A is a top perspective view of another embodiment of positionable holder 10. In the embodiment of FIG. 5A, stem 14 includes a recess 100 which receives opposing protrusions 102 which act as locking mechanisms. As stem 14 is pivoted from the low profile position to the standard implantation position, C-ring 101 spreads protrusions 102 and snap into recesses 100. C-ring 101 is secured at region 99. The remainder of ring 101 is free to bend and flex. The hinging/pivot mechanism can be any appropriate method. The relative shapes of recess 100 and protrusions 102 provide a locking mechanism to secure holder 10 in the standard implantation position as shown in FIG. 5A.

Figure 5B:
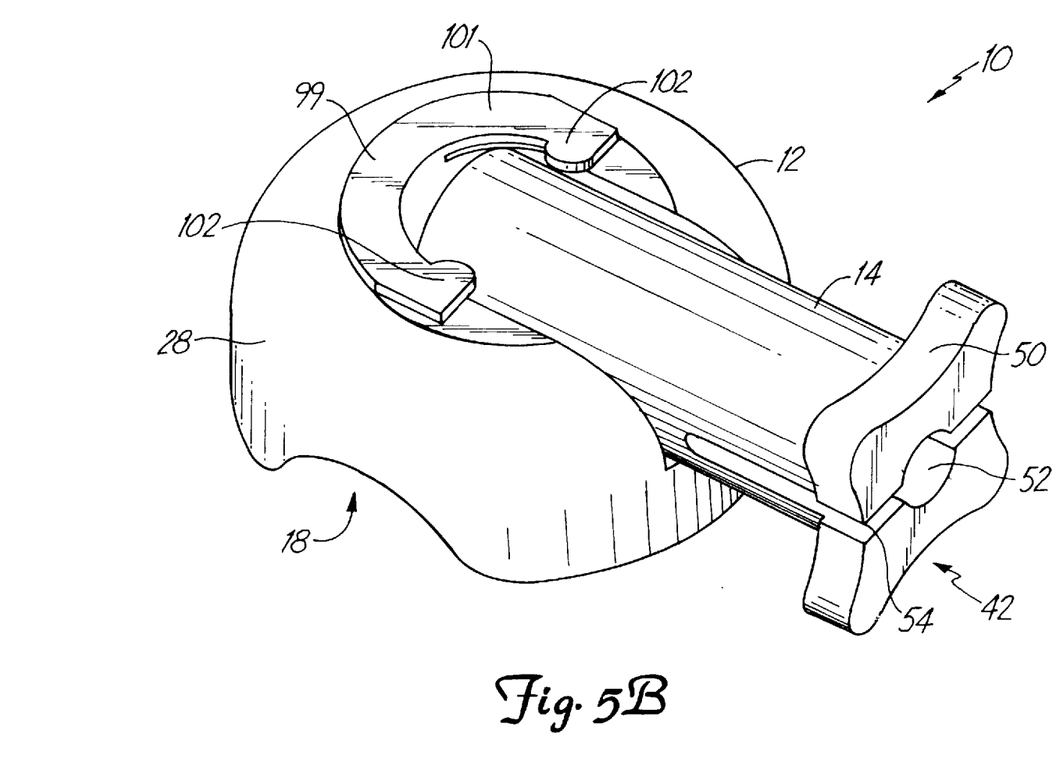
FIG. 5B is a top perspective view of the positionable holder of FIG. 5A shown in a low profile delivery position.

FIG. 5B is a top perspective view of positionable holder 10 in accordance with the embodiment of Figure 5A showing stem 14 in the low profile position. In this position, stem 14 fits into open portion 24. Recess portion 106 of stem 14 abuts stop 74 of holder body 12. Protrusions 102 may be modified to act as a locking mechanism to secure stem 14 in a low profile position.

Figure 6A:
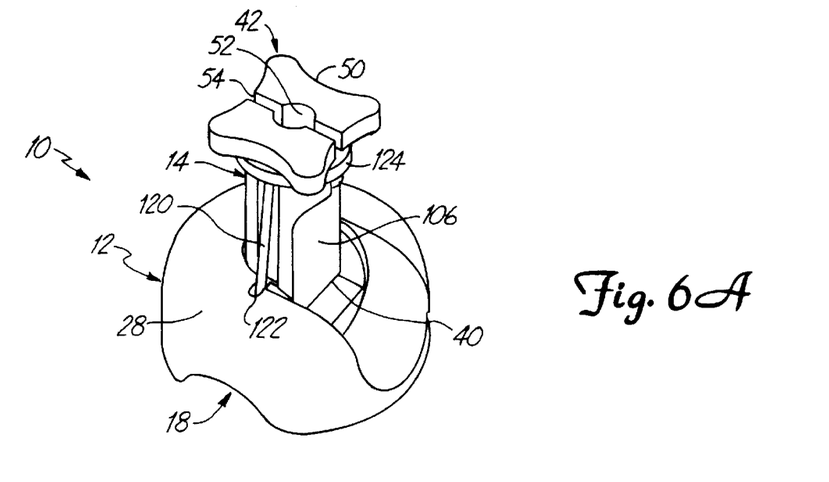
FIGS. 6A, 6B and 6C are top perspective, side plan and top plan views, respectively, of a positionable holder in accordance with another embodiment.
Figure 6B:
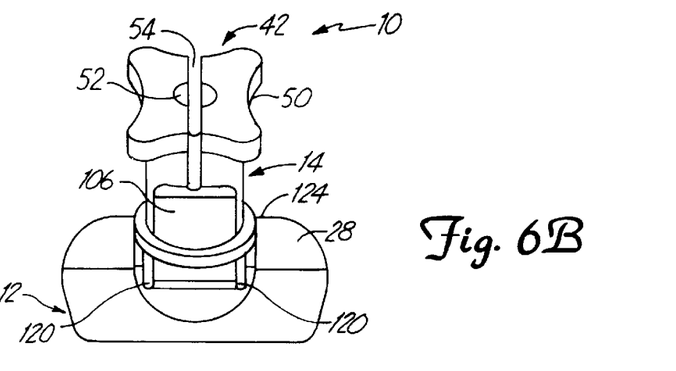
Figure 6C:
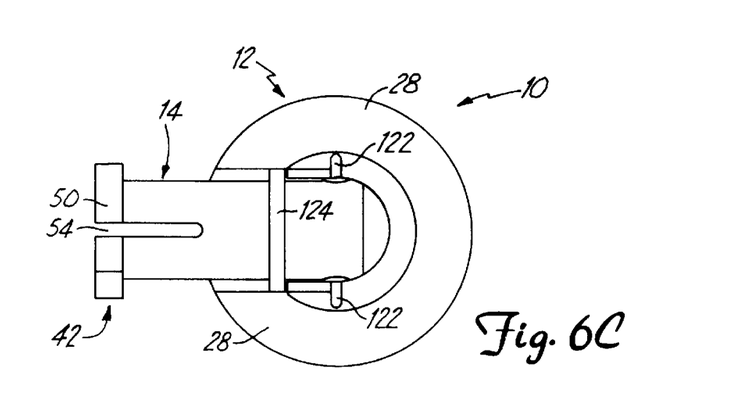

FIGS. 6A, 6B and 6C show top perspective, side plan and top plan views, respectively, of a positionable holder 10 in accordance with another embodiment shown in three different positions. In the embodiments of FIGS. 6A through 6C, elongated spring members 120 are received in slots 122 on holder body 12. Elongated spring members 120 are coupled to stem 14 near proximal end 42. As shown in FIG. 6A, when spring member 120 is engaged with slot 122, stem 14 is secured in the standard implantation position. However, by moving collar 124 which encircles stem 14 in a direction from proximal end 42 of stem 14 toward distal end 40, spring members 120 are pushed inward, toward stem 14, to thereby disengage slots 122, as shown in FIG. 6B. FIG. 6B also shows stem 14 articulated at an angle somewhere between the standard implantation position and the low profile implantation position. FIG. 6C shows positionable holder 10 with stem 14 in the low profile implantation position. Note that by adding additional slots 122, stem 14 may be selectively locked in multiple positions relative to holder body 12.

Figure 7:
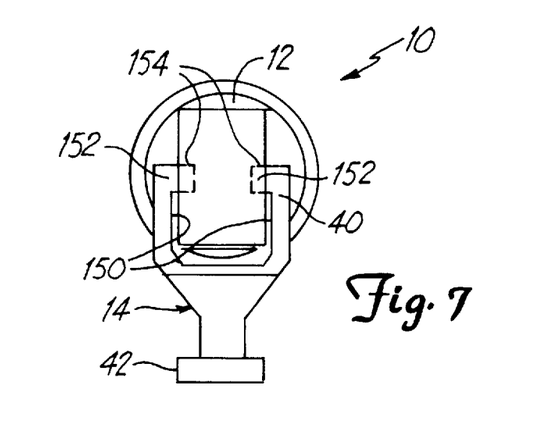
FIG. 7 is a top plan view of a positionable holder in accordance with another embodiment.

FIG. 7 is a top plan view of positionable holder 10 in accordance with another embodiment. In the embodiment of FIG. 7, stem 14 includes elongated members 150 which carry extensions 152. Extensions 152 fit into recesses 154 formed in holder body 12. Holder body 12 is secured to stem 14 between extensions 152 which may pivot in recesses 154.

Figure 8:
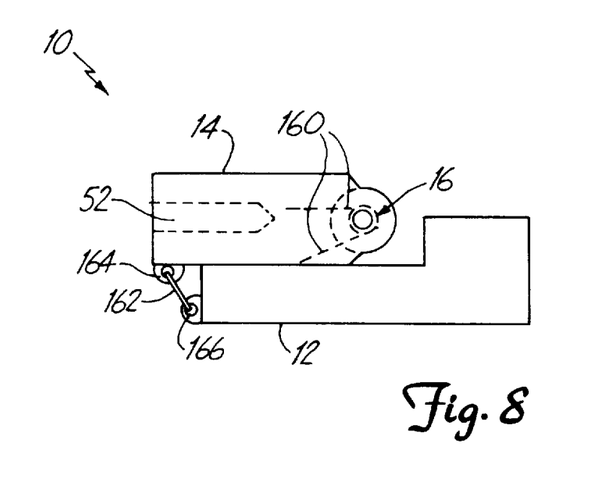
FIG. 8 is a side plan view of a locking mechanism for use with a positionable holder.

FIG. 8 is a side plan view showing one example of a locking mechanism in accordance with the present invention for use with positionable holder 10. In FIG. 8, stem 14 is spring loaded by torsional spring member 160 about a pivot formed at pivot pin 16. A suture 162 is secured to stem 14 at suture attachment 164 and to holder body 12 at suture attachment 166. In FIG. 8, stem 14 is shown in the low profile implantation position. When suture 162 is cut, spring 160 urges stem 14 into the upright, standard implantation position.

Figure 9:
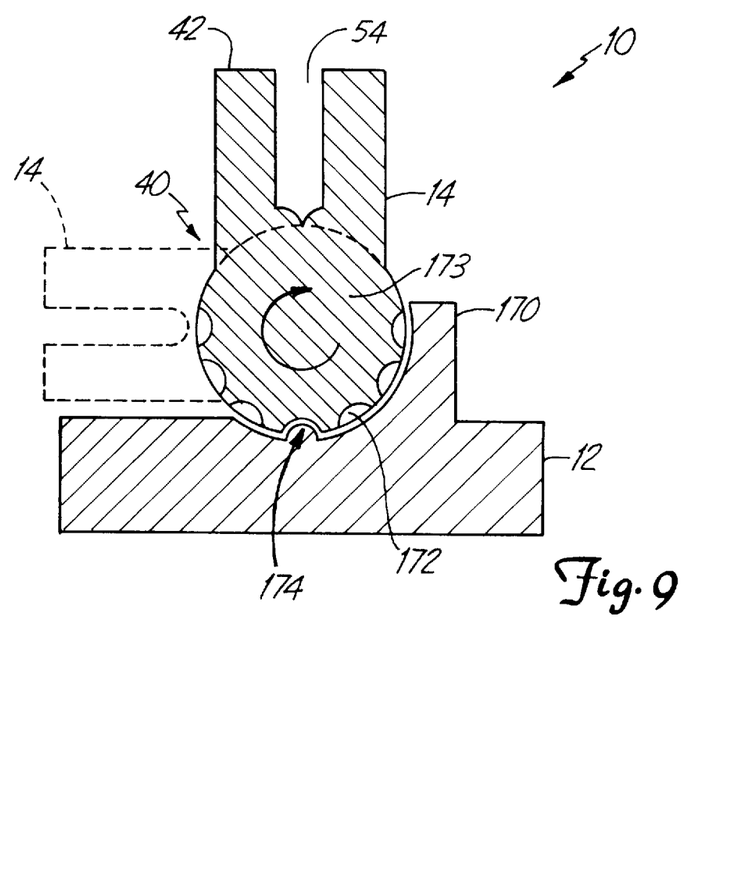
FIG. 9 is a side cross-sectional view of a locking mechanism in accordance with another embodiment.

FIG. 9 is a cross-sectional view of another embodiment of a pivoting and locking mechanism for positionable holder 10 in accordance with the invention. A socket wall 170 extends around distal portion 40 of stem 14. This embodiment could encompass a captive ball and socket design that allows infinite articulation of stem 14 along multiple axes. Further, it will be understood that, although a ball and socket allows two degrees of freedom, it also constitutes one type of pivot. If discreet positioning is desired, this can be accomplished using a plurality of recesses or indentations 172 formed around a circumference of ball 173 of distal portion 40 of stem 14 and are shaped to receive nub 174. Nub 174 and indentations 172 secure stem 14 at a number of angular positions between the standard implantation position shown in FIG. 9 and the low profile implantation position shown in phantom in FIG. 9. A slight elastic deformation of nub 174 allows movement between adjacent indentations 172. Further, the position of indentations 172 and nub 174 could easily be reversed.

Figure 10:
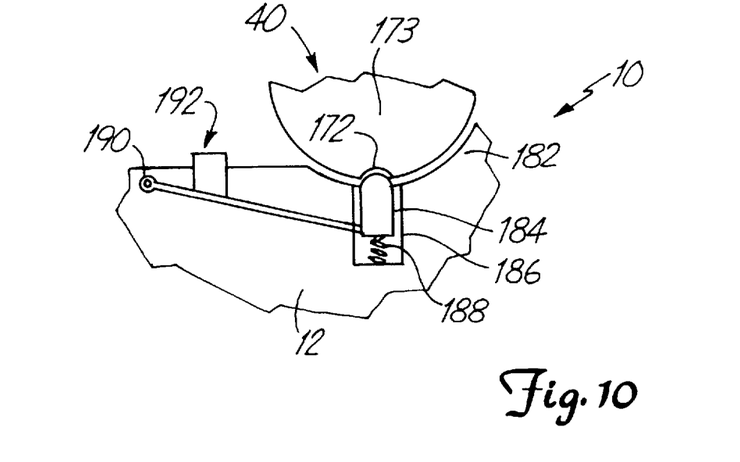
FIG. 10 is a side cross-sectional view of a locking mechanism in accordance with another embodiment of the invention.

FIG. 10 is a side cross-sectional view of a locking mechanism which could be used in combination with the pivoting mechanism in FIG. 9 or any other embodiment herein for use with positionable holder 10. As shown in FIG. 10, distal portion 40 of stem 14 includes a ball 173 which is received in a socket 182 formed in holder body 12. A nub 184 carried in recess 186 is received in an indentation 172 and urged in a direction toward ball 173 by spring 188, thereby locking stem 14 in a selected position relative to holder 12. A pin 190 is positioned to actuate nub 184 when button 192 is pressed to thereby disengage nub 184 from indentation 172 formed in ball 173. Depressions or recesses may be used as alternatives to the nubs or indentations shown herein.

Figure 11:
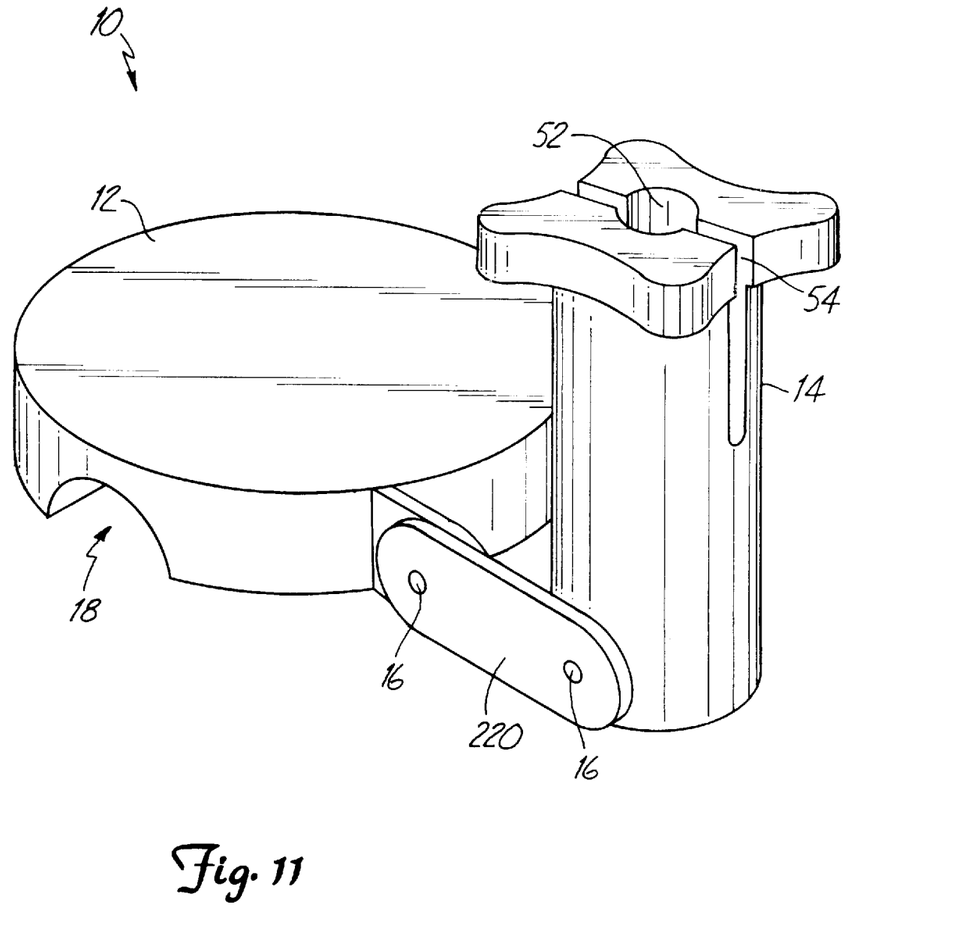
FIG. 11 is a perspective view of a positionable holder in accordance with another embodiment.

FIG. 11 is a perspective view of holder 10 in accordance with another embodiment. In the embodiment of FIG. 11, stem 14 is offset from the axis of holder 10 and is carried between extensions 220. Multiple pivot points may be possible as extensions 220 can be movably attached to both body 12 and stem 14 and locked in place by any of the locking mechanisms described herein. Note that this particular embodiment provides a very low profile when in the low profile delivery position.

Figure 12:
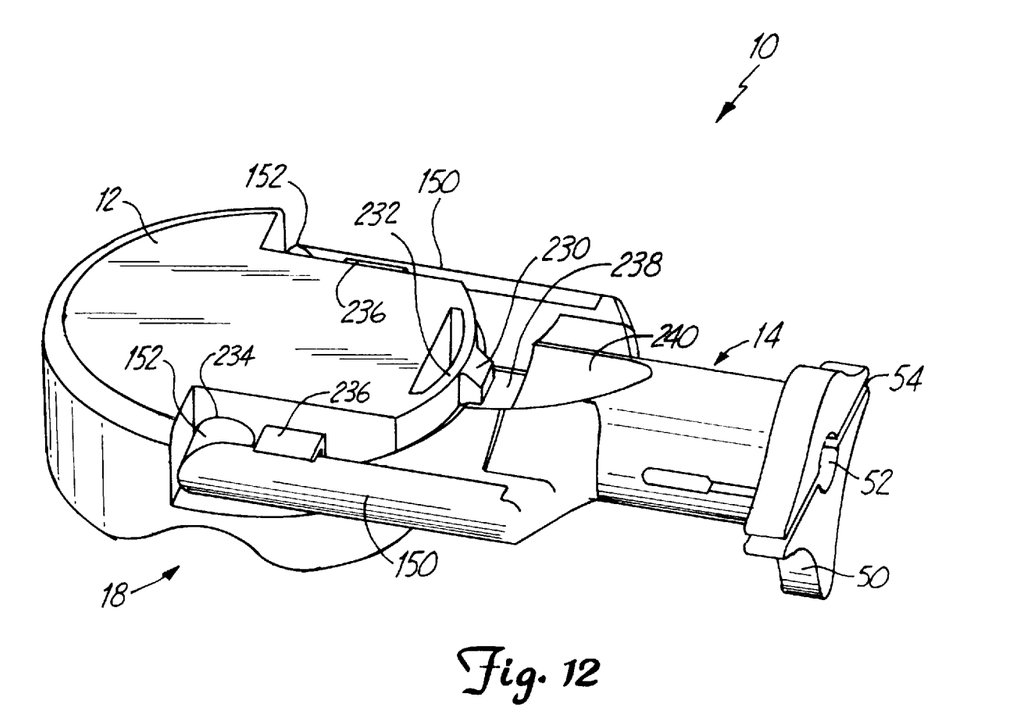
FIG. 12 is a top perspective view of a positionable holder in accordance with another embodiment

FIG. 12 is a top perspective view of holder 10 in accordance with another embodiment which is similar to the pivoting embodiment shown in FIG. 7. In the embodiment of FIG. 12, holder body 12 includes a tab 230 carried on beam 232. Stem 14 includes elongated members 150 which carry extensions 152. A spring member 234 is wrapped around extensions 152 and is coupled to elongated members 150 at tab 236. Stem 14 includes tab stop 238 aligned with tab 230 to maintain stem 14 in the low profile implantation position as shown in FIG. 12. However, an elongated surgical member may be pressed against tab 230 by moving the elongated surgical member along recessed guide area 240. This action causes tab 230 to disengage tab stop 238 whereby spring member 234 causes stem 14 to articulate into the standard implantation position. Those skilled in the art will recognize that members 150 may snap into any portion of body 12 such as along sides of body 12. Further, any type of moveable attachment may be used.

Holder bodies in accordance with the present invention may be moved relative to the stem using any appropriate technique. Further, during a minimally invasive implantation, the surgeon may articulate the positionable holder back to the standard implantation position after introducing the positionable holder and the prosthesis into the chest cavity of the patient. This articulation may be performed using any technique. One simple technique is to use an elongated surgical instrument to push the holder body into position. However, an actuator which extends along the handle and provides a direct linkage to the holder body could also be used to control remote positioning. Such remote positioning may be through any appropriate technique including elongated members, sutures, twisting motions, spring elements, etc.

Preferably, the holder body and stem of the present invention are made of polyphenylsulfone, such as Radel®. This material is biocompatible, durable and well suited for injection molding techniques which help reduce manufacturing costs. However, other materials and manufacturing techniques are considered within the scope of the present invention.

Those skilled in the art will recognize that the invention may be implemented in any appropriate manner and those described herein are merely preferred embodiments. More specifically, any type of holder body shape or design may be implemented along with any type of stem or other element which supports the holder body during implantation. Further, any appropriate mechanism to allow articulation or relative movement between the stem and holder body may be employed as may any locking mechanism. As used herein, pivoting attachment mechanism is intended to include any attachment technique which allows articulation of the stem relative to the holder body, even those which have never been explicitly described. Similarly, the term locking mechanism is intended to include anything which may be used to lock or selectively lock the relative positions of the stem and holder body. Those skilled in the art will recognize that there are numerous attachment mechanisms which may be employed and locking mechanisms which will operate within the spirit and scope of the present invention.

The invention may also be used with bioprosthetic valves and annuloplasty repair devices. In general, the invention allows relative movement between a stem and a body of a holder which may be locked in position. The invention allows articulation through the holder using existing tools and can be used for both standard and low profile implantation techniques. The invention can also be used to adjust the prosthesis to conform to the anatomy of the patient as necessary. Torque may be applied through the holder to rotate the prosthesis. In the standard implantation position, the holders may be retrofit for use in existing packages.

Although the present invention has been described with reference to preferred embodiments workers skilled in the art will recognize that changes may be made in form and detail without departing from the spirit and scope of the invention.

What is claimed is:

1. A holder for a cardiovascular prosthetic device, comprising:

a single piece holder body adapted to contact generally opposed sides of a circumference of couple to the prosthetic device;

a stem extending in a longitudinal direction having a distal end and a proximal end used to manipulate the prosthetic device during implantation, the stem having a handle opening in the proximal end the handle opening extending in the longitudinal direction and adapted to releasably couple to an elongated handle upon application of a separation force directed in the longitudinal direction;

a pivotable attachment mechanism which pivotably couples the distal end of the stem to the holder body allowing the stem to pivot relative to the holder body about the attachment mechanism; and a locking mechanism adjacent the holder body and coupled to the holder body and to the distal end of the stem, the locking mechanism to selectively maintain the stem in at least one of a plurality of fixed angular positions relative to the holder body.

2. The holder of claim 1 wherein the pivotable attachment mechanism provides relative movement between the holder body and the stem enabling articulation between the standard implantation position and a low profile delivery position.

3. The holder of claim 2 wherein the stem forms an angle of generally 90° with a plane of the prosthetic device in the standard implantation position.

4. The holder of claim 2 wherein the stem forms an angle of generally 0° with a plane of an annulus of the holder body in the low profile delivery position.

5. The holder of claim 1 wherein the pivotable attachment mechanism includes a pin which extends through pin openings in the stem and the holder body.

6. The holder of claim 1 wherein the pivotable attachment mechanism comprises a pivot.

7. The holder of claim 6 wherein the pivot comprises a pin received in an opening.

8. The holder of claim 1 wherein the pivotable attachment mechanism comprises a ball received in a socket.

9. The holder of claim 1 wherein the prosthetic device comprises a heart valve prosthesis and the holder is adapted to engage the heart valve prosthesis.

10. The holder of claim 1 wherein the prosthetic device comprises an annuloplasty repair prosthesis and the holder is adapted to engage the annuloplasty repair prosthesis.

11. The holder of claim 1 wherein at least one of the plurality of fixed angular positions comprise a standard implantation position.

12. The holder of claim 1 wherein at least one of the plurality of fixed angular positions comprise a low profile delivery position.

13. The holder of claim 1 wherein the locking mechanism comprises a nub received in a recess.

14. The holder of claim 1 wherein the locking mechanism comprises a suture.

15. The holder of claim 1 wherein the locking mechanism comprises a spring member received in a slot.

16. The holder of claim 15 including a collar coupled to the stem for releasably engaging the spring member with the slot.

17. The holder of claim 1 wherein the locking mechanism includes a plurality of positioning detents.

18. The holder of claim 1 including a spring member coupled to the stem and applying a force relative to the stem and the holder body.

* * * * *

UNITED STATES PATENT AND TRADEMARK OFFICE
CERTIFICATE OF CORRECTION

PATENT NO. : 5,814,101
DATED : September 29, 1998
INVENTOR(S) : Margaret A. Wallner et al.

It is certified that error appears in the above-indentified patent and that said Letters Patent is hereby corrected as shown below:

```
Col. 7, line 10, after "end" insert --,--
```

Signed and Sealed this

Twenty-fourth Day of August, 1999

Attest:

Q. TODD DICKINSON

*Attesting Officer*   *Acting Commissioner of Patents and Trademarks*